United States Patent
Metz-Stavenhagen et al.

(10) Patent No.: US 6,193,755 B1
(45) Date of Patent: *Feb. 27, 2001

(54) SPINAL CAGE ASSEMBLY

(75) Inventors: Peter Metz-Stavenhagen, Bad Wildungen; Bernd Robioneck, Preetz, both of (DE)

(73) Assignee: Howmedica GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/935,097

(22) Filed: Sep. 25, 1997

(30) Foreign Application Priority Data

Sep. 26, 1996 (DE) .......................................... 296 16 778 U

(51) Int. Cl.[7] ........................................................ A61F 2/44
(52) U.S. Cl. ...................................................... 623/17.11
(58) Field of Search ............................ 623/17, 16, 17.11, 623/17.15; 606/60

(56) References Cited

U.S. PATENT DOCUMENTS

| | | | |
|---|---|---|---|
| 4,657,550 | 4/1987 | Daher | 623/17 |
| 4,820,305 | 4/1989 | Harms et al. | 623/16 |
| 5,015,247 | 5/1991 | Michelson | 606/61 |
| 5,405,391 | 4/1995 | Hednerson et al. | 623/17 |
| 5,571,192 | * 11/1996 | Schonhoffer | 623/17 |
| 5,609,637 | 3/1997 | Biedermann | 623/17 |
| 5,702,449 | * 12/1997 | McKay | 623/17 |
| 5,702,451 | 12/1997 | Biedermann | 623/17 |
| 5,702,455 | * 12/1997 | Saggar | 623/17 |
| 5,776,197 | * 7/1998 | Rabbe et al. | 623/17 |
| 5,989,290 | * 11/1999 | Biedermann et al. | 623/17.11 |
| 6,015,436 | * 1/2000 | Schonhoffer | 623/17.11 |

FOREIGN PATENT DOCUMENTS

| | | | |
|---|---|---|---|
| 4323034 | 7/1994 | (DE) . | |
| 4409392A | 9/1995 | (DE) . | |
| 4423257A | 1/1996 | (DE) . | |
| 195 00 170 | 2/1996 | (DE) . | |
| 195 04 867 | 2/1996 | (DE) . | |
| 195 09 317 | 9/1996 | (DE) . | |
| 296 16 778 U | 3/1998 | (DE) . | |
| 0188954 | 7/1986 | (EP) . | |
| 0268115 | 5/1988 | (EP) . | |
| 0307741 | 3/1989 | (EP) . | |
| 0637440 | 2/1995 | (EP) . | |
| WO 96/37170 | * 11/1996 | (EP) | 623/17.11 |
| 9418913 | 9/1994 | (WO) . | |
| 9526164 | 10/1995 | (WO) . | |

* cited by examiner

*Primary Examiner*—David H. Willse
*Assistant Examiner*—Suzette J. Jackson
(74) *Attorney, Agent, or Firm*—Lerner, David, Littenberg, Krumholz & Mentlik, LLP

(57) ABSTRACT

A spinal cage assembly has an inner sleeve-shaped tubular body which telescopes into or through an outer tubular sleeve-shaped body from either a first or second end thereof. Each inner and outer sleeve is made of one-piece construction made of a physiologically compatible metal. Both sleeve-shaped bodies have multiple holes therein and can be secured at different heights relative to one another. At least one of the sleeve-shaped bodies has two edges which form a different angle of between about 3° and about 6° with respect to the transverse axis of the sleeve-shaped bodies. An edge having a different angle is exposed depending on which end of the inner body is inserted into or through the outer body.

30 Claims, 3 Drawing Sheets

SPINAL CAGE ASSEMBLY

BACKGROUND OF THE INVENTION

The invention relates to a spinal cage assembly.

There are known spinal cord implants that are designed as hollow bodies and driven individually or in pairs into the area of adjacent vertebrae to achieve effective fusion of adjacent vertebrae. Such implants are known, for example, from European Patent 307,741 B1, German Patent 4,416,605 C1, German Patent 4,323,956 C1, European Patent Application 637,440 A1, World Patent Application 95/26164, U.S. Pat. No. 5,015,247 or German Utility Model 29,600,879. The hollow design of the implants serves to accommodate bone material, thus achieving better fusion.

Furthermore, so-called spinal cage assemblies have become known that are inserted after vertebral resection and replace the missing vertebra. Such a spinal cage assembly is disclosed, for example, in German Utility Model 9,107,494, European Patent 188,954 or European Patent 535,215. With the known spinal cage assemblies, the point of action on the vertebrae is relatively centrally located in an area that is relatively soft. Therefore, there is the danger of the spinal cage assembly digging into the vertebra.

There is a similar danger with spinal cage assemblies made of a relatively thin-walled braid.

An object of this invention is a spinal cage assembly that will permit effective support, while at the same time building up new bone substance between the vertebrae.

This and other objects are achieved by the device of the invention.

SUMMARY OF THE INVENTION

According to this invention, a spinal cage assembly has a sleeve-shaped body made of a physiologically compatible material, which has a relatively thick wall that is suitable for transmitting relatively high forces, and which also permits support on the adjacent vertebrae with a relatively low surface pressure. This support is especially effective when the diameter of the sleeve-shaped body is designed so that the wall is supported in the cortical area of the vertebrae because the cortical area is known to be the hardest area of bone.

Also according to the invention, the end faces or leading edges are irregularly designed and the sleeve-shaped body is secured against rotation. The sleeve-shaped body has perforations in its wall through which bone material can be introduced into the interior of the sleeve-shaped body.

According to the invention in another embodiment, the irregular edge of the sleeve-shaped body lies in a plane that forms an angle to the transverse axis of the sleeve-shaped body which is an angle between 3° and 6°. This permits adaptation to the prevailing anatomical conditions.

According to the invention in another embodiment, the leading edge may be shaped with teeth and gaps between the teeth, for example with the teeth having flat surfaces at the tips so that the teeth are prevented from digging deeply into the vertebra. The gaps between the teeth preferably have a rounded contour, with the gaps between the teeth forming relatively sharp edges with the tip surfaces of the teeth.

For inserting a sleeve-shaped body, preferably a tool is used, which has a relatively long shaft and has a threaded stem at the free end. The threaded stem may be engaged with a threaded hole in the sleeve-shaped body to insert the sleeve-shaped body into the space of the resected vertebra in the proper position between two neighboring vertebrae.

The height of the spinal cage assembly depends on the height of the resected vertebra or the remaining distance between neighboring vertebrae and the position of the vertebra in the spinal cord. Therefore, the known spinal cage assemblies are usually adjustable in length. To permit adjustment with the spinal cage assembly according to this invention as well, one embodiment of the invention also provides a second sleeve-shaped body that accommodates the first sleeve-shaped body by telescoping it inward and is shaped like the inner sleeve-shaped body. In addition, both sleeve-shaped bodies have holes that can be aligned with each other and into which threaded screws can be inserted to secure the two sleeve-shaped bodies relative to each other. In this position, the inner sleeve-shaped body projects slightly out of the outer. If a pair of holes is provided according to another embodiment of the invention, two distance steps can be adjusted. Together with the height of the inner body, this thus yields four height levels, which is completely sufficient for most surgical cases encountered. The height is adjusted before inserting the implant, so that difficult manipulations are not necessary for a height adjustment in situ.

According to another embodiment of the invention, it is also conceivable to apply a force element, etc., between the sleeve-shaped telescoping bodies to achieve automatic adjustability in height. For example, a prestressed spring may be provided that moves the two sleeve-shaped bodies apart for elongation purposes when a suitable locking device is released. However, it is also conceivable to provide a different force element.

It is conceivable to provide a square or polygonal cross section for the sleeve-shaped body. However, a circular cross section in adaptation to the contour of the vertebrae is preferable.

As mentioned above, the tool for inserting the sleeve-shaped body has a relatively long shaft. According to one embodiment of the invention, a sleeve may be mounted on the free end of this shaft so it can rotate and is supported on a shoulder of the shaft, and on the free end it has a concave recess that approximately matches the outside contour of the sleeve-shaped body. In this way, the transverse forces that must be applied by the tool when inserting the sleeve body are not applied only through the relatively thin threaded stem but also through the sleeve.

This invention is explained in greater detail below on the basis of figures.

DESCRIPTION OF THE PREFERRED EMBODIMENTS

DETAILED DESCRIPTION OF THE DRAWINGS

A spinal cage assembly 10 shown in FIGS. 1 through 4 has an outer sleeve-shaped body 12 and an inner sleeve-shaped body 14. Both sleeve-shaped bodies 12 and 14 have a relatively thick wall, are made of a metal, preferably titanium, that is tolerated by the body, and have a circular cross section. The dimensions are such that inner sleeve-shaped body 14 can be telescoped into outer body 12. The diameters of outer body 12 and inner body 14 are also selected so that when inserted between neighboring vertebrae, they are essentially supported on the cortical area. The spinal cage assembly disclosed here is suitable primarily for lumbar vertebrae.

Figure 1:
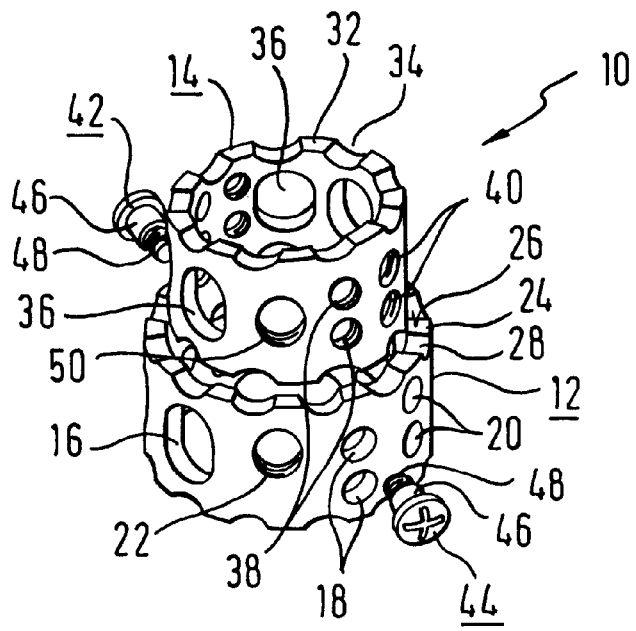
FIG. 1 shows a perspective view of a spinal cage assembly according to this invention.
Figure 3:
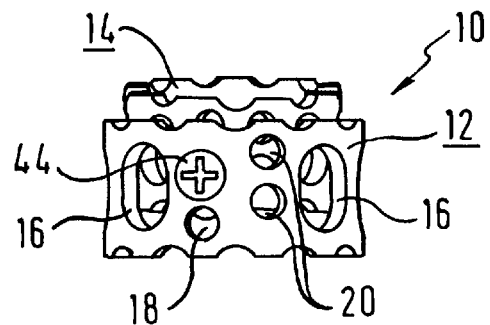
FIG. 3 shows a side view of the spinal cage assembly according to FIG. 1 in the opposite direction.

The outer sleeve-shaped body 12 has two pairs of perforations in the shape of elongated holes that can be seen as 16 in FIG. 1 or 3. These are for inserting bone material.

Furthermore, the outer sleeve-shaped body 14 has eight pairs of radial holes 18 and 20, such that one of each pair is arranged above the other of that pair. The holes of one pair are arranged one above the other along an axis parallel to the longitudinal axis of that pair of sleeve-shaped body 12. The holes of pairs 18, 20, arranged side by side, are offset relative to each other, which can be seen especially well in FIGS. 2 and 3.

Finally, sleeve-shaped body 12 has two threaded holes, one of which is shown as 22. The purpose of the individual holes in the wall of sleeve-shaped body 12 is explained in greater detail below.

Sleeve-shaped body 12 has uniformly spaced teeth 24 in the circumferential direction on the upper and lower sides, with a free upper side 26. Between the teeth there are arc-shaped gaps 28 between the teeth, forming relatively sharp edges with the teeth in the area of the upper faces 26. Therefore, the structure of the upper and lower sides of the sleeve-shaped body prevents twisting after implantation and also secures it against rotation.

Figure 4:
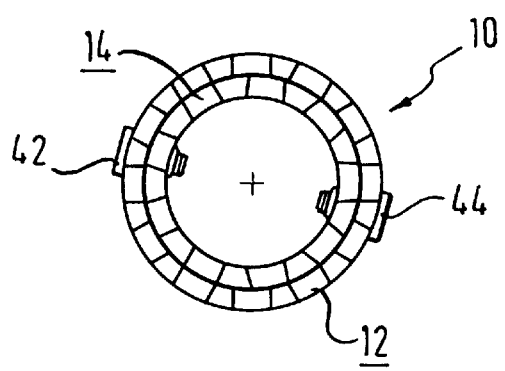
FIG. 4 shows a top view of the spinal cage assembly according to FIG. 1 in an assembled state.

The inner sleeve-shaped body 14 is shaped like the outer sleeve-shaped body 12 and has toothed upper and lower sides with teeth 32 and rounded gaps 34 between the teeth. The inner body 14 also has pairs of perforations 36 which are also elongated and can be aligned approximately with perforations 16. Furthermore, inner body 14 has four pairs of threaded holes arranged one above the other, with two pairs of holes 38, 40 shown in FIG. 2. The holes of each pair are always arranged vertically, one above the other. The holes of one pair can be aligned with holes of a pair 18, 20 of the outer body 12. Two screws 42, 44 can be inserted into holes 18, 20, with threadless section 46 also being inside a hole 18, 20, while threaded section 48 can be screwed into the respective threaded hole 38, 40 to secure inner and outer bodies 14, 12 with respect to each other, as shown in FIG. 4. Since the holes of pairs 18, 20 and pairs 38, 40 are arranged so they are staggered in height relative to each other, different positions of the inner body relative to the outer body can be established. For example, if the bottom hole of pair 38 is aligned with the bottom hole of pair 18, then the inner body 14 projects minimally out of the outer body 12. But if the upper hole of pair 40 is aligned with the upper hole of pair 20, the inner body 14 projects maximally out of the outer body 12.

Figure 2:
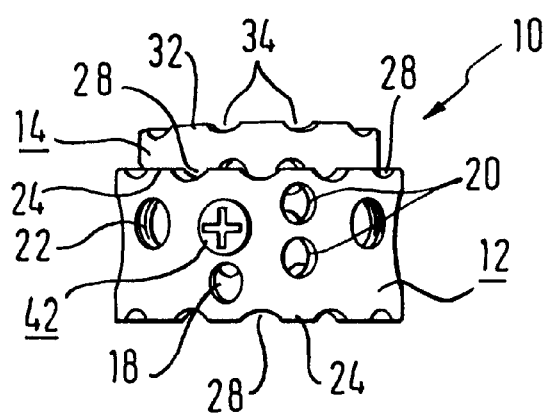
FIG. 2 shows a side view of the spinal cage assembly according to FIG. 1 in a first direction.

Other threaded holes 50, one of which is shown in FIG. 1 and two in FIG. 2, are also provided in inner body 14. Threaded holes 50, like threaded holes 22, also serve to provide a connection with a tool according to FIGS. 6 through 8, which will be discussed further below.

Figure 5:
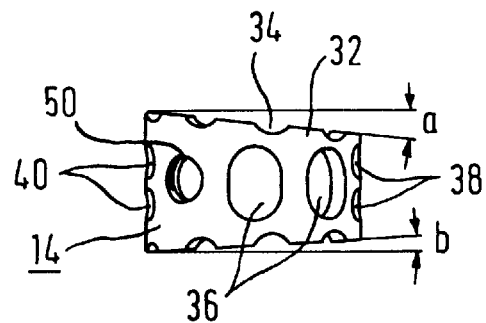
FIG. 5 shows a side view of the inner sleeve body of the spinal cage assembly according to FIG. 1.

The inner body 14 has an inclined upper side, as indicated in the diagram in FIG. 3. The inner body 14 is shown separately in FIG. 5. This shows that the upper side forms an angle a of 6° to the transverse axis and the lower side forms an angle b of 3°. Depending on which end of inner body 14 is inserted into the outer, a corresponding inclined surface results at the upper side. This permits an adaptation to the respective anatomical condition.

It is self-evident that either an inner body 14 or an outer body 12 can also be used individually by itself.

Figure 6:
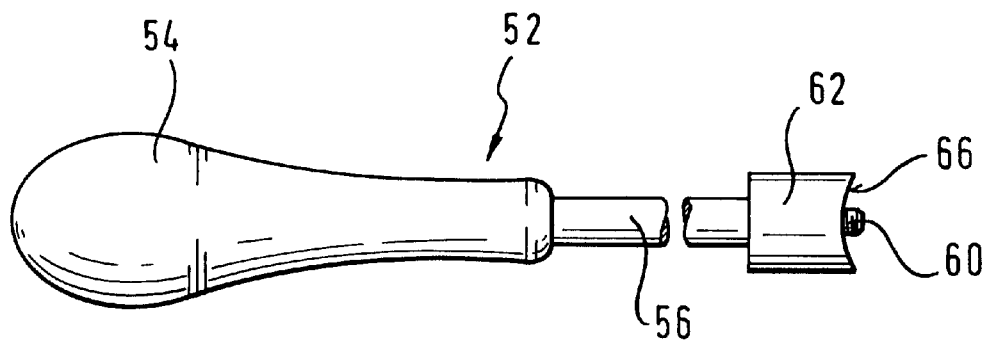
FIG. 6 shows a diagrammatic illustration of a tool for handling the spinal cage assembly according to FIG. 1.
Figure 7:
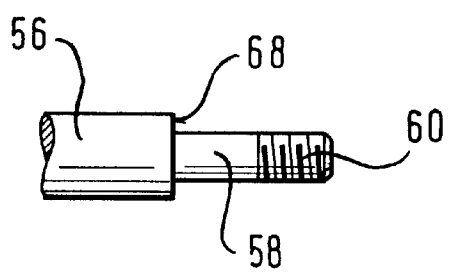
FIG. 7 shows a detail from the diagram according to FIG. 6.
Figure 8:
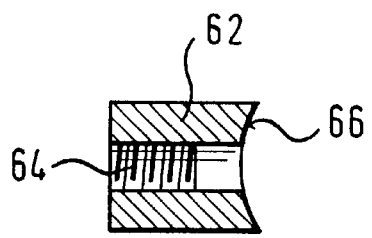
FIG. 8 shows a section through the sleeve of the tool according to FIG. 6.

FIGS. 6 through 8 show a suitable insertion tool 52 having a handle 54, a shaft 56 with a length of 20 cm, for example, and a stem 58 with a smaller diameter on the distal end than on the proximal end. As shown in FIG. 7, stem 58 has a threaded section 60 on the free end. On this stem sits a sleeve 62 in whose hole is provided an internal threaded section 64 that extends to the left end but stops a distance away from the right end. The right end or free end of sleeve 62 has a concave recess 66 that is adapted to the rounded contour of inner body 14 or outer body 12. In assembly, sleeve 62 is screwed over threaded section 60 of stem 58 and then at one end comes to a stop against a shoulder 68 in shaft 56. Sleeve 62 is thus mounted so it can rotate, but the thread prevents axial displacement and allows it to be removed only by unscrewing. In the connection with the spinal cage assembly according to FIGS. 1 through 5, threaded section 60 of stem 58 is screwed into threaded hole 22 or threaded hole 50, where sleeve 62 is rotated so that it engages and fits with the outside of the sleeve wall. Therefore, effective forces can be transmitted from shaft 56 to the spinal cage assembly.

What is claimed is:

1. A spinal cage assembly comprising an inner sleeve-shaped tubular body which telescopes into or through an outer tubular sleeve-shaped body from either a first or second end thereof, each inner and outer sleeve is of one-piece construction made of a physiologically compatible metal, wherein both sleeve-shaped bodies have multiple holes therein, and can be secured at different heights relative to one another; wherein at least one of the sleeve-shaped bodies has two edges which form a different angle of between about 3° and about 6° with respect to the transverse axis of the sleeve-shaped bodies such than an edge having a different angle is exposed depending on which end of said inner body is inserted into or through said outer body.

2. A spinal cage assembly according to claim 1, wherein said sleeves have circumferential ends with an irregular edge having teeth and gaps between the teeth.

3. A spinal cage assembly according to claim 2, wherein said teeth have tips having flat surfaces.

4. A spinal cage assembly according to claim 3, wherein said gaps between the teeth each form an arc-shaped curve, with the gaps between the teeth forming relatively sharp edges with the flat surfaces.

5. A spinal cage assembly according to claim 4, wherein said holes provided in said wall are elongated and have a longitudinal axis which is approximately parallel to the longitudinal axis of the sleeve-shaped body.

6. A spinal cage assembly according to claim 5, wherein at least one threaded hole is provided in said wall for insertion of a positioning tool having a stem having a threaded end.

7. A spinal cage assembly according to claim 1, wherein locking devices are provided to secure together inner body and outer body in their respective positions with respect to each other.

8. A spinal cage assembly according to claim 7, wherein the outer body has at least one radial threaded hole for engagement with a positioning tool having a threaded stem.

9. A spinal cage assembly according to claim 8, wherein said outer sleeve-shaped body has a wall provided with radial perforations.

10. A spinal cage assembly according to claim 9, wherein the inner and outer bodies have a circular cross section.

11. A spinal cage assembly according to claim 9, wherein said locking devices are threaded screws each having a head and a shaft which has a threaded section, and between the head and the threaded section is provided a cylindrical threadless section whose diameter is approximately the same as the diameter of the radial holes in said outer sleeve-shaped body.

12. The spinal cage assembly of claim 1 wherein the inner body is of one-piece construction and the outer body is of one-piece construction, and both bodies have substantially the same height.

13. The spinal cage assembly of claim 1, wherein said outer body has at least two radial holes that are offset in the circumferential direction, the inner body has at least two threaded holes that are offset in the circumferential direction and can be aligned with the radial holes of the outer body in such a way that the inner body projects partially out of the outer body, and wherein the outer body also has an irregular edge on each end face and threaded screws can be inserted into the holes or and can secure the inner body and outer body with respect to each other.

14. The spinal cage assembly of claim 13, wherein at least two pairs of radial holes and threaded holes are provided, and wherein the holes of each pair are arranged one above the other along an axis parallel to the longitudinal axis of the respective body.

15. The spinal cage assembly of claim 1, wherein locking devices are provided to secure together inner body and outer body in their respective positions with respect to each other.

16. The spinal cage assembly of claim 15, wherein the outer body has at least one radial threaded hole for engagement with a positioning tool having a threaded stem.

17. The spinal cage assembly of claim 16, wherein said outer sleeve-shaped body has a wall provided with radial perforations.

18. The spinal cage assembly of claim 17, wherein the inner and outer bodies have a circular cross section.

19. The spinal cage assembly of claim 17, wherein said locking devices are threaded screws each having a head and a shaft which has a threaded section, and between the head and the threaded section is provided a cylindrical threadless section whose diameter is approximately the same as the diameter of the radial holes in said outer sleeve-shaped body.

20. The spinal cage assembly of claim 1 wherein both of the inner and outer sleeve-shaped bodies have first and second end faces both forming irregular edges.

21. A spinal cage assembly comprising an inner sleeve-shaped tubular body which telescopes into or through an outer tubular sleeve-shaped body, each inner and outer sleeve is of one-piece construction made of a physiologically compatible metal, wherein both sleeve-shaped bodies have multiple holes therein, and can be secured at different heights relative to one another, wherein at least one of the sleeve-shaped bodies has two edges which form a different angle of between about 3° and about 6° with respect to the transverse axis of the sleeve-shaped bodies such that an edge having a different angle is exposed depending on which end of said inner body is inserted into or through said outer body.

22. A spinal cage assembly according to claim 21, wherein at least one threaded hole is provided in said outer sleeve-shaped body for insertion of a positioning tool having a stem having a threaded end.

23. A spinal cage assembly according to claim 21, wherein the inner sleeve-shaped body telescopes into the outer sleeve-shaped body and can be secured therein at different heights with respect to each other.

24. A spinal cage assembly according to claim 21, wherein said outer sleeve-shaped body has at least two radial holes that are offset in the circumferential direction, the inner sleeve-shaped body has at least two threaded holes that are offset in the circumferential direction and can be aligned with the radial holes of the outer body in such a way that the inner body projects partially out of the outer body, and wherein the outer body and inner body have end faces with an irregular edge on each end face and threaded screws can be inserted into the holes and can secure the inner body and outer body with respect to each other.

25. A spinal cage assembly according to claim 21, wherein at least two pairs of radial holes and threaded holes are provided, and wherein the holes of each pair are arranged one above the other along an axis parallel to a longitudinal axis of the respective body.

26. A spinal cage assembly according to claim 20, wherein locking devices are provided to secure together inner body and outer body in their respective positions with respect to each other.

27. A spinal cage assembly according to claim 26, wherein the inner and outer bodies have a circular cross section.

28. A spinal cage assembly according to claim 26, wherein said locking devices are threaded screws each having a head and a shaft which has a threaded section, and between the head and the threaded section is provided a cylindrical threadless section whose diameter is approximately the same as the diameter of the radial holes in said outer sleeve-shaped body.

29. The spinal cage assembly of claim 21 wherein both of the inner and outer sleeve-shaped bodies have first and second end faces both forming irregular edges.

30. A spinal cage assembly according to claim 21, wherein said sleeve-shaped bodies have circumferential ends with an irregular edge having teeth and gaps between the teeth.

* * * * *

UNITED STATES PATENT AND TRADEMARK OFFICE
CERTIFICATE OF CORRECTION

PATENT NO. : 6,193,755 B1
DATED : February 27, 2001
INVENTOR(S) : Metz-Stavenhagen et al.

It is certified that error appears in the above-identified patent and that said Letters Patent is hereby corrected as shown below:

Column 6,
Line 32, "20" should read -- 21 --.

Signed and Sealed this

Twenty fifth Day of September, 2001

Attest:

Nicholas P. Godici

NICHOLAS P. GODICI
Attesting Officer     Acting Director of the United States Patent and Trademark Office